US011547652B2

(12) United States Patent
Mahe et al.

(10) Patent No.: US 11,547,652 B2
(45) Date of Patent: Jan. 10, 2023

(54) COMBINATION PRODUCTS AND COSMETIC COMPOSITIONS FOR CONTROLLING SKIN DISORDERS AND SKIN AGING THAT AFFECT KERATINOCYTES AND/OR FIBROBLASTS AND THE DERMIS

(71) Applicant: NUTRICOS Technologies, Clichy (FR)

(72) Inventors: Yann Mahe, Ste Genevieve des Bois (FR); Carole Bru, Courbevoie (FR)

(73) Assignee: NUTRICOS TECHNOLOGIES, Clichy (FR)

( * ) Notice: Subject to any disclaimer, the term of this patent is extended or adjusted under 35 U.S.C. 154(b) by 681 days.

(21) Appl. No.: 15/322,512

(22) PCT Filed: Jun. 30, 2015

(86) PCT No.: PCT/EP2015/064863
§ 371 (c)(1),
(2) Date: Dec. 28, 2016

(87) PCT Pub. No.: WO2016/001233
PCT Pub. Date: Jan. 7, 2016

(65) Prior Publication Data
US 2018/0214365 A1     Aug. 2, 2018

(30) Foreign Application Priority Data

Jun. 30, 2014 (FR) ........................................ 1456146
Jun. 30, 2014 (FR) ........................................ 1456161

(51) Int. Cl.
| *A61K 8/73* | (2006.01) |
| *A61K 8/60* | (2006.01) |
| *A61Q 19/08* | (2006.01) |
| *A61K 8/68* | (2006.01) |
| *A61L 27/20* | (2006.01) |
| *A61K 8/65* | (2006.01) |
| *A61Q 19/00* | (2006.01) |

(52) U.S. Cl.
CPC ................ *A61K 8/735* (2013.01); *A61K 8/60* (2013.01); *A61K 8/65* (2013.01); *A61K 8/68* (2013.01); *A61K 8/73* (2013.01); *A61L 27/20* (2013.01); *A61Q 19/007* (2013.01); *A61Q 19/08* (2013.01); *A61K 2800/88* (2013.01); *A61K 2800/884* (2013.01); *A61K 2800/92* (2013.01); *A61L 2400/06* (2013.01)

(58) Field of Classification Search
CPC .......... A61K 8/735; A61K 8/60; A61K 38/39; A61K 8/65; A61L 2800/92; A61L 2400/06
See application file for complete search history.

(56) References Cited

U.S. PATENT DOCUMENTS

| 5,391,373 | A | 2/1995 | Mausner | |
| 6,979,458 | B1 | 12/2005 | Martin et al. | |
| 2002/0025921 | A1* | 2/2002 | Petito | A61K 38/39 514/25 |
| 2002/0068718 | A1* | 6/2002 | Pierce | A23K 50/20 514/54 |
| 2003/0068297 | A1 | 4/2003 | Jain | |
| 2003/0152642 | A1 | 8/2003 | Stone | |
| 2007/0009576 | A1* | 1/2007 | Stillman | A23L 2/38 424/439 |
| 2007/0092469 | A1* | 4/2007 | Jacobs | A61K 31/7024 514/23 |
| 2008/0063677 | A1 | 3/2008 | Long et al. | |
| 2010/0310654 | A1* | 12/2010 | Jacono | A61P 17/00 424/474 |
| 2010/0323984 | A1 | 12/2010 | Piccirilli et al. | |
| 2011/0160137 | A1* | 6/2011 | Kim | A61P 17/16 514/17.2 |
| 2012/0021046 | A1* | 1/2012 | Capomacchia | A61K 8/602 424/450 |
| 2012/0141611 | A1* | 6/2012 | Landes | A61K 36/76 424/727 |
| 2013/0137656 | A1* | 5/2013 | Moutet | A61K 8/63 514/54 |

(Continued)

FOREIGN PATENT DOCUMENTS

| BG | 1273 U1 * | 2/2010 | |
| CN | 1319536 C * | 6/2007 | ........... B65G 47/847 |

(Continued)

OTHER PUBLICATIONS

ChemBook (downloaded from https://www.chemicalbook.com/ProductChemicalPropertiesCB6522052_EN.htm on Jan. 31, 2019 (Year: 2019).*
Tammi (Hyaluronan Accumulation in Wounded Epidermis: A Mediator of Keratinocyte Activation, Journal of Investigative Dermatology 2009, 129: 1858-1860) (Year: 2009).*
Chembook (downloaded from https://www.chemicalbook.com/ProductList_en.aspx?kwd=GLuCOSAMINE&a=United%20States&left=True#J_Condition on Jan. 31, 2019) (Year: 2019).*

(Continued)

Primary Examiner — Lianko G Garyu
(74) Attorney, Agent, or Firm — Polsinelli PC

(57) ABSTRACT

This invention relates to a cosmetic combination product comprising a first cosmetic composition comprising glucosamine or one of the salts thereof, a second cosmetic composition comprising hyaluronic acid, and possibly a third cosmetic composition comprising collagen, a cosmetic composition comprising glucosamine or one of the salts thereof, hyaluronic acid, and possibly collagen, the uses thereof, in particular for inducing the synthesis of hyaluronic acid and as such combat aging of the skin affecting the keratinocytes and/or the fibroblasts and the dermis, as well as a cosmetic method that implements these combination products and compositions.

29 Claims, 2 Drawing Sheets

(56) References Cited

U.S. PATENT DOCUMENTS

Figure 1:
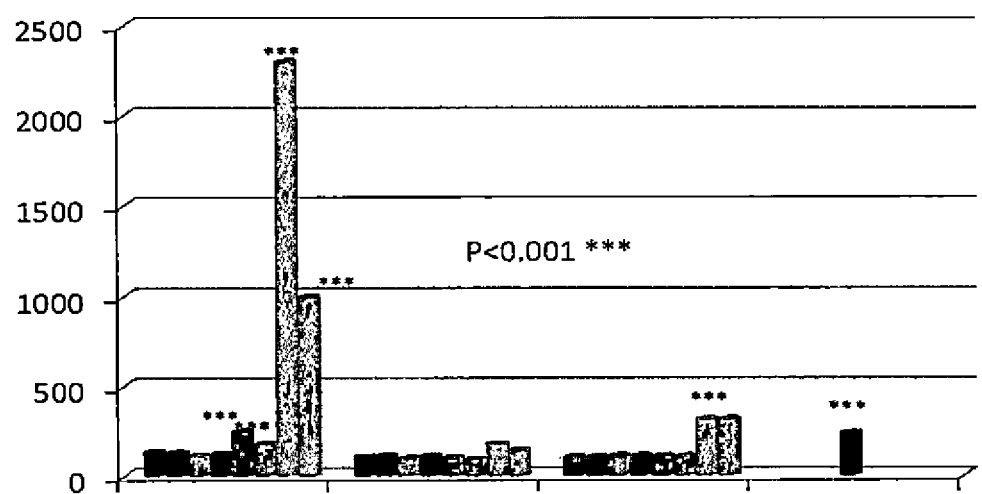

| | | | |
|---|---|---|---|
| 2013/0137854 A1 | 5/2013 | den Hoed | |
| 2013/0165845 A1 | 6/2013 | Piergallini et al. | |
| 2014/0079749 A1* | 3/2014 | Pinsky | A61K 38/39 |
| | | | 424/401 |
| 2016/0110459 A1 | 4/2016 | Jamrog | |

FOREIGN PATENT DOCUMENTS

| | | | | |
|---|---|---|---|---|
| CN | 101232891 A | | 7/2008 | |
| CN | 101690727 A | | 4/2010 | |
| CN | 102349867 A | * | 2/2012 | |
| EP | 1075836 A2 | | 2/2001 | |
| EP | 1384482 A1 | | 1/2004 | |
| EP | 1932530 A1 | | 6/2008 | |
| EP | 2033689 | | 3/2009 | |
| EP | 2033689 A1 | | 3/2009 | |
| FR | 2867073 | | 9/2005 | |
| WO | WO-2008/113819 A1 | | 3/2007 | |
| WO | WO-2012/120290 A2 | | 9/2012 | |
| WO | WO-2014041528 A2 | * | 3/2014 | A61K 8/31 |

OTHER PUBLICATIONS

Fisher et al. ("Restoration of the basement membrane after wounding: a hallmark of young human skin altered with aging", J. Cell Commun. Signal. (2018) 12:401-411) . (Year: 2018).*

Schwartz ("Ingestion of BioCell Collagen®, a novel hydrolyzed chicken sternal cartilage extract; enhanced blood microcirculation and reduced facial aging signs", Clinical Interventions in Aging, 2012, pp. 267-273) (Year: 2012).*

Edwards et al. ("Review of long-term adverse effects associated with the use of chemically-modified animal and nonanimal source hyaluronic acid dermal fillers", Clinical Interventions in Aging 2007:2(4) 509-519). (Year: 2007).*

John et al., ("Perspectives in the selection of hyaluronic acid fillers for facial wrinkles and aging skin", Patient Preference and Adherence 2009:3 225-230). (Year: 2009).*

Gold, "Use of hyaluronic acid fillers for the treatment of the aging face", Clinical Interventions in Aging, 2007, 369-376 (Year: 2007).*

Natural Factors, Extra Strength Joint Care—MINTEL, Record ID 1369680, Aug. 2010.

PK Benelux, Bone & Joint Formula 7—MINTEL, Record ID 141618, Oct. 2010.

Jamieson Laboratories, Arthrimin GS Glucosamine Chondroitin Effervescent—MINTEL, Record ID 1333413, Jun. 2010.

Swanson Ultra Vita-Lanne, All-In-One Nutrient Formula Dietary Supplement—MINTEL, Record ID 1631948, Sep. 2011.

Kalman et al., "Effect of a natural extract of chicken combs with a high content of hyaluronic acid (Hyal-Joint®) on pain relief and quality of life in subjects with knee osteoarthritis: a pilot randomized double-blind placebo-controlled trial", Nutrition Journal 2008, 7:3, 2008, pp. 1-9.

* cited by examiner

COMBINATION PRODUCTS AND COSMETIC COMPOSITIONS FOR CONTROLLING SKIN DISORDERS AND SKIN AGING THAT AFFECT KERATINOCYTES AND/OR FIBROBLASTS AND THE DERMIS

CROSS REFERENCE TO RELATED APPLICATIONS

This application is a National Phase filing under 35 U.S.C. § 371 of PCT/EP2015/064863 filed on Jun. 30, 2015; and this application claims priority to Application No. 1456161 filed in France on Jun. 30, 2014 under 35 U.S.C. § 119; and this application claims priority to Application No. 1456146 filed in France on Jun. 30, 2014 under 35 U.S.C. § 119. The entire contents of each application are hereby incorporated by reference.

This invention relates to a cosmetic combination product comprising a first cosmetic composition comprising glucosamine or one of the salts thereof, a second cosmetic composition comprising hyaluronic acid, and possibly a third cosmetic composition comprising collagen, a cosmetic composition comprising glucosamine or one of the salts thereof, hyaluronic acid, and possibly collagen, the uses thereof, in particular for inducing the synthesis of hyaluronic acid and as such combat aging of the skin affecting the keratinocytes and/or the fibroblasts and the dermis, as well as a cosmetic method that implements these combination products and compositions.

Hyaluronic acid is a macromolecule comprised of a repetitive chain of a sugar pattern that has substantial properties in terms of hydration and tissue support. The skin, which contains about 50% of the hyaluronic acid of the human body, is one of the richest organs in hyaluronic acid. The renewal of the hyaluronic acid in the skin is rapid and practically daily. With aging, its renewal is altered.

There is therefore a need to assist the organism in renewing the quantity of hyaluronic acid, in particular in order to prevent the sagging of subcutaneous matrix tissue, the appearance of wrinkles or the loss of hydration of the skin.

As such, many cosmetic products propose creams containing hyaluronic acid in order to assist in maintaining a hydration of the skin and combat the aging thereof.

However, the attempts at reintroducing hyaluronic acid orally have often shown to be unsuccessful. Indeed, this large polysaccharide molecule does not efficiently pass through the intestinal barrier. In addition, in light of its biochemical nature, it is quickly degraded.

In order to overcome this problem, a very commonly used aesthetic technique consists in directly repulping the wrinkles or certain cutaneous zones by filling them with hyaluronic acid polymers using a syringe (the term "fillers" is used).

This technique however has the disadvantage of having to be renewed about every six months as the newly injected hyaluronic acid also degrades over time.

The technical problem at the basis of this invention therefore consists in being able to stimulate the endogenous synthesis of hyaluronic acid and as such prolong its synthesis in the skin, in particularly orally, for example as a supplement of already existing topical interventions or aesthetic injections.

Glucosamine is commonly used, in particular orally, to combat osteoarthritis. Indeed, glucosamine is one of the two natural constituents of hyaluronic acid, with the latter corresponding to a polymeric chain of disaccharide dimers comprised of N-Acetyl glucosamine on the one hand and of D-glucuronic acid on the other hand, linked together by a saccharide bond.

Glucosamine, contrary to the large molecules of hyaluronic acid, is very quickly bioavailable and is found in the blood circulation quickly after ingestion. It persists therein even after several hours (Persiani S. et al. Glucosamine oral bioavailability and plasma pharmacokinetics after increasing doses of crystalline glucosamine sulfate in man. OsteoArthtitis and Cartilage. 2005; 13: 1041-1049).

Glucosamine could as such be useful as a oral precursor in the endogenous synthesis of hyaluronic acid for joint health. It is indeed known to induce the synthesis of hyaluronic acid, in particular through implants of bone cells in vitro (Ultterlinden et al. Glucosamine increases hyaluronic acid production in human osteoarthritic synovium explants. BMC musculoskeletal disorders 2008, 9:120-125).

In order to respond to the issues linked more specifically to the synthesis of hyaluronic acid in the skin, the inventors of this invention have shown very surprisingly and unexpectedly that an association between glucosamine or one of the salts thereof and hyaluronic acid was able to induce the synthesis of hyaluronic acid by skin cells: keratinocytes, while an association between glucosamine or one of the salts thereof and hyaluronic acid was able to induce the synthesis of hyaluronic acid by cells of the dermis: fibroblasts, but in the presence of collagen.

Indeed, although the inventors of this application observed that the use of glucosamine or one of the salts thereof made it possible to induce the synthesis of hyaluronic acid by keratinocytes, they did however observe that human fibroblasts were refractory to this effect In addition, they also observed that the contact of the keratinocytes with the hyaluronic acid alone did not stimulate the proper synthesis of the latter and that hyaluronic acid alone or an extract of cartilage comprising hyaluronic acid and collagen, did not stimulate the synthesis of hyaluronic acid, by contact with fibroblasts.

As such, the inventors of this invention revealed very surprisingly that only the association of glucosamine or one of the salts thereof with hyaluronic acid synergistically and substantially stimulated the synthesis of hyaluronic acid by keratinocytes and that only the association of glucosamine or one of the salts thereof with hyaluronic acid and collagen synergistically and substantially stimulated the synthesis of hyaluronic acid by fibroblasts.

Based on the effects obtained, these synergistic combinations therefore make it possible to respectively combat the aging of the skin that affects the keratinocytes, in particular the signs of aging linked to the loss of matrix tissue, and the aging of the skin affecting the fibroblasts, in particular against the signs of aging linked to the loss of dermal connective tissue.

As such, this invention concerns a cosmetic combination product for an administration that is simultaneous, separated or spread over time, comprising a first cosmetic composition comprising glucosamine or one of the salts thereof and a second cosmetic composition comprising hyaluronic acid, and possibly furthermore a third cosmetic composition comprising collagen.

This invention also relates to a cosmetic composition comprising glucosamine or one of the salts thereof and hyaluronic acid, and possibly furthermore collagen.

The term "cosmetic combination product" or "cosmetic composition" means a substance or a preparation intended to be placed in contact with the various surface portions of the human body, in particular the epidermis, hair and nail systems, lips and external genital organs, or with the teeth and the mucous membranes of the oral cavity with a view exclusively or mainly of cleaning them, embellishing them, perfuming them, modifying the aspect of them, protecting them, maintaining them in good conditions or correcting body odors. Reference is also, for example made to a nutritional composition, for example a dietary supplement.

The term "dietary supplement," here means a food of which the purpose is to supplement the normal diet and which is a concentrated source of nutrients, i.e. vitamins and/or minerals, and/or other substances with a nutritional or physiological effect, alone or in combination, marketed in dose form, namely forms such as gel capsules, lozenges, tablets, soft capsules, pills and other similar forms, as well as powder sachets to be diluted, liquid ampoules, bottles with a dropper and other similar forms of liquid preparations or in beverage form.

This invention does not relate to the therapy field.

The terms "salts" of glucosamine means any salt of glucosamine can be formulated into a cosmetic composition such as, for example glucosamine sulfate or glucosamine hydrochloride. In particular, the glucosamine salt included in cosmetic combination products and cosmetic compositions according to the invention is glucosamine sulphate.

The hyaluronic acid comprised in cosmetic combination products and cosmetic compositions according to the invention can be of various origins. It can for example be obtained biotechnologically such as resulting from a bacterial synthesis. In particular, the hyaluronic acid comprised in cosmetic combination products and cosmetic compositions according to the invention is of bacterial origin. In certain embodiments, hyaluronic acid may be comprised in any element comprising or capable of producing, as for example cartilage from an edible source from fish or mammals such as pork, beef or poultry, and more preferably from chicken.

The collagen comprised in cosmetic combination products and cosmetic compositions according to the invention can be of various origins. It may be comprised in any element comprising or capable of producing, as for example cartilage, preferably cartilage from an edible source from fish or mammals such as pork, beef or poultry, and more preferably from chicken. Collagen can also come from a biotechnological production method and in particular be obtained from bacterial strains.

According to an embodiment of the cosmetic combination products according to the invention comprising glucosamine or one of the salts thereof, hyaluronic acid and collagen, hyaluronic acid and collagen are comprised in the same cosmetic composition and come from a cartilage extract in particular chicken.

According to an embodiment of the cosmetic combination products according to the invention comprising glucosamine or one of the salts thereof, hyaluronic acid and collagen, hyaluronic acid and collagen come from a cartilage extract such as a cartilage extract of chicken.

In particular, the cosmetic combination products or cosmetic compositions according to the invention comprise from 0.0001 to 99% of glucosamine or one of the salts thereof, in particular from 0.001 to 50%, and more particularly from 0.1 to 10%.

Also in particular, the cosmetic combination products or cosmetic compositions according to the invention, more particularly the cosmetic combination products or cosmetic compositions comprising glucosamine or one of the salts thereof, hyaluronic acid and collagen, comprise at least 0.1% hyaluronic acid, in particular at least 2% and more particularly at least 4% by weight relative to the total weight of the the cosmetic combination product or cosmetic composition.

Also in particular, the cosmetic combination products or cosmetic compositions according to the invention, more particularly the cosmetic combination products or cosmetic compositions comprising glucosamine or one of the salts thereof and hyaluronic acid, comprise from 0.1 to 99% hyaluronic acid, in particular from 10% to 30% and more particularly from 16 to 25%.

More particularly, the cosmetic combination products or cosmetic compositions according to the invention, more particularly the cosmetic combination products or cosmetic compositions comprising glucosamine or one of the salts thereof, hyaluronic acid and collagen, comprise at least 0.1% collagen, preferably 0.1% to 99% collagen, in particular from 1 to 60%, and more particularly from 1 to 10% by weight relative to the total weight of the the cosmetic combination product or cosmetic composition.

According to an embodiment of this invention, the cosmetic compositions of the cosmetic combination products according to the invention are intended to be administered orally.

According to another embodiment of this invention, the cosmetic compositions of the cosmetic combination products according to the invention are intended to be administered topically.

According to yet another embodiment of this invention, in cosmetic combination products according to the invention, the cosmetic composition comprising glucosamine or one of the salts thereof is to be administered orally and the cosmetic composition(s) comprising hyaluronic acid and possibly collagen are intended to be administered topically.

According to yet another embodiment of this invention, in the cosmetic combination products according to the invention, the compositions comprising hyaluronic acid and collagen are intended to be administered orally and the composition comprising glucosamine or one of the salts thereof is to be administered topically.

According to an embodiment of this invention, in cosmetic combination products according to the invention comprising cosmetic compositions comprising glucosamine or one of the salts thereof, hyaluronic acid and collagen, the compositions comprising glucosamine or one of the salts thereof and collagen are intended to be administered orally and the composition comprising hyaluronic acid is to be administered topically.

According to a separate embodiment of this invention, in cosmetic combination products according to the invention, the cosmetic composition(s) comprising glucosamine or one of the salts thereof and possibly collagen are intended to be administered orally and the cosmetic composition comprising hyaluronic acid is a filler cosmetic composition intended to be administered into the skin, in particular in the framework of the preparation of fillers with hyaluronic acid.

The term "filling composition" or "filler" means a composition to fill wrinkles (wrinkles and permanent grooves), which is in particular in the form of gel.

As such, the cosmetic compositions of the combination product according to the invention are all administered orally, all administered topically, or administered by different routes of administration, as exemplified above, the latter may independently from each other be administered simultaneously, separately or in a staggered manner.

Moreover, according to an embodiment of this invention, cosmetic compositions comprising glucosamine or one of the salts thereof and hyaluronic acid and possibly further comprising the collagen, according to this invention, are intended to be administered orally.

Moreover, according to another embodiment of this invention, cosmetic compositions comprising glucosamine or one of the salts thereof and hyaluronic acid and possibly further comprising collagen, according to this invention, are intended to be administered topically, in particular in the form of patches.

According to an embodiment of this invention, the cosmetic combination product or the cosmetic composition does not comprise active ingredients other than those listed hereinabove.

For oral administration, the cosmetic compositions according to the invention, including those forming part of the cosmetic combination products according to the invention, may be in any suitable form, and may take the form of a sugar-coated pill, a gel capsule, a suspension, a gel, an emulsion, an oral solution, a tablet to be swallowed or to be chewed, a capsule in particular a soft or hard capsule, granules to be dissolved, syrup, tablet or a drinkable ampoule.

It may preferably be in the form of a capsule, hard or soft, preferably in the form of a soft capsule.

In particular, a composition according to the invention can be implemented in all forms of food supplements or compacted or not. The powders can be diluted with water or in soda. According to an embodiment, a composition according to the invention administered orally can be formulated as a sugar-coated pill, gel capsule, gel, emulsion, tablet, capsule, hydrogel, powder compact or not, suspension or liquid solution.

The oral compositions may be either in anhydrous form, or in aqueous form.

A composition in accordance with the invention can be formulated with routine excipients for such oral compositions, such as dietary supplements, namely in particular fatty and/or aqueous constituents, moistening agents, thickeners, preservatives, texture, flavor and/or coating agents, antioxidants, preservatives and colorants used routinely in the field of nutrition.

In the case of compositions suitable for oral administration, the use of an ingestible support is favored. The ingestible substrate may be of various natures according to the type of composition in question.

The formulation of such compositions may be carried out by any conventional method known to those skilled in the art.

For topical application to the skin, the cosmetic compositions according to the invention may take the form in particular of aqueous or oily solutions or dispersions of the lotion or serum type, emulsions of liquid or semi-liquid consistency of the milk type, obtained by dispersing a fatty phase in an aqueous phase (O/W) or conversely (W/O), or suspensions or emulsions of soft type cream or aqueous or anhydrous gel type, or alternatively microcapsules or microparticles, or vesicular dispersions of ionic and/or nonionic type or foams. These compositions are prepared according to routine methods.

These cosmetic compositions can for example constitute creams for cleaning/removing make-up, make-up, protection, treatment or care for the face (for example day creams, night creams, makeup-removing creams, foundation creams, sunscreen), fluid foundations, make-up removing milks, body milks for protection or care, anti-sun milks, lotions, gels or foams for skin care, such as cleansing lotions, sunscreen lotions, artificial tanning lotions, bath compositions, deodorant compositions comprising a bactericidal agent, aftershave gels or lotions.

The compositions can also be packaged in the form of an aerosol composition also comprising a pressurized propellant.

The cosmetic compositions according to the invention may also contain usual additives in the cosmetic field, such as hydrophilic or lipophilic gelling agents, hydrophilic or lipophilic additives, preservatives, antioxidants, solvents, perfumes, bulking agents, filters, odor absorbers and dyes. The quantities of these various additives are those conventionally used in the cosmetic field, and for example vary from 0.01 to 10% of the total weight of the composition. These additives, depending on their nature, may be introduced in the fatty phase in the aqueous phase and/or in lipid spheres.

Of course, those skilled in the art will take care to choose these possible excipients and formulation agents and/or the quantity thereof, such that the advantageous properties of the active constituents of the cosmetic composition product according to the invention or the cosmetic composition according to the invention are not, or are substantially not, altered by the addition under consideration.

For example, a cosmetic combination product according to the invention has the following composition:
Tablet Product for Oral Administration:
Glucosamine sulfate 250 mg
Hyaluronic Acid 100 mg
Excipients QSP 380 mg For example, a cosmetic combination product according to the invention has the following composition:
Tablet Product for Oral Administration:
Glucosamine sulfate 125 mg
Hyaluronic Acid 60 mg
Collagen 5 mg
Excipients QSP 380 mg For example, a cosmetic composition according to the invention has the following composition:
Topical Composition (Moisturizing Liquid Serum):
Hyaluronic Acid 0.05%
Glucosamine sulfate 5%
Glycerin 2%
Mineral oil 2.5%
Scent 0.015%
Demineralized water QSP 50 mL For example, another cosmetic composition according to the invention has the following composition:
Topical Composition (Moisturizing Liquid Serum):
Hyaluronic acid 5%
Glucosamine sulfate 2%
Collagen 0.4%
Glycerin 2%
Mineral oil 2.5%
Scent 0.015%
Demineralized water QSP 50 mL As mentioned hereinabove, in an entirely surprising and unexpected way, the inventors of this invention have demonstrated that the cosmetic combination products and cosmetic compositions according to the invention make it possible to induce the synthesis of hyaluronic acid.

More particularly, said combination products and compositions are useful for inducing skin or epidermal synthesis of hyaluronic acid, in particular on the dermis and/or the dermal epidermal junction.

More particularly, said combination products and compositions are useful to induce the epidermal synthesis of hyaluronic acid in the dermal epidermal junction when the combination products or the cosmetic composition comprise glucosamine and hyaluronic acid.

More particularly, said combination products and compositions are useful to induce the cutaneous synthesis of hyaluronic acid on the dermis and the dermal epidermal junction when the combination products or the cosmetic composition comprise glucosamine, hyaluronic acid and collagen.

As such, this invention also relates to the cosmetic use of a cosmetic combination product as defined in the framework of this invention or of a cosmetic composition such as defined in the framework of this invention to induce the synthesis of hyaluronic acid, in particular to induce the cutaneous or epidermal synthesis of hyaluronic acid, more particularly in the dermis and/or the dermal epidermal junction.

Still more particularly, in the framework of this invention, the hyaluronic acid synthesis is induced by the keratinocytes of the skin when the combination products or the cosmetic composition comprise glucosamine and hyaluronic acid or is induced by skin fibroblasts of the dermis when the combination products or the cosmetic composition comprise glucosamine, hyaluronic acid and collagen.

As such, this invention also relates to the cosmetic use of a combination product according to the invention or of a cosmetic composition according to the invention to enhance the dermal epidermal junction and/or the synthesis of hyaluronic acid in the dermis and the connective tissue of the dermal-epidermal junction.

In particular, the cosmetic composition product according to the invention or the cosmetic composition according to the invention is useful in reinforcing the dermal epidermal junction and/or synthesis of connective tissue of the dermal-epidermal junction when the combination product or cosmetic composition comprises glucosamine and hyaluronic acid.

In particular, the cosmetic composition product according to the invention or the cosmetic composition according to the invention is useful in reinforcing the dermal epidermal junction and/or synthesis of hyaluronic acid by the dermis and the connective tissue of the dermal-epidermal junction when the combination product or cosmetic composition comprises glucosamine, hyaluronic acid and collagen.

In particular, the cosmetic combination products and the cosmetic compositions according to the invention make it possible to combat the aging of the skin affecting keratinocytes when the combination product or the cosmetic composition comprises glucosamine and hyaluronic acid, or aging of the skin affecting fibroblasts when the combination product or the cosmetic composition comprises glucosamine, hyaluronic acid and collagen.

More particularly, the cosmetic combination products and the cosmetic compositions according to the invention make it possible to combat the signs of aging linked to the loss of matrix tissue, dryness and dry and thin appearance of the skin, particularly when the combination product or the cosmetic composition comprises glucosamine and hyaluronic acid.

Particularly, the cosmetic combination products and the cosmetic compositions according to the invention make it possible to combat the signs of aging linked to the loss of matrix tissue, to the appearance of wrinkles and fine lines and skin sagging, particularly when the combination product or the cosmetic composition comprises glucosamine and hyaluronic acid.

Particularly, the cosmetic combination products and the cosmetic compositions according to the invention make it possible to combat the signs of aging linked to the loss of conjunctive and dermal tissue, particularly when the combination product or the cosmetic composition comprises glucosamine, hyaluronic acid and collagen.

Particularly, the cosmetic combination products and the cosmetic compositions according to the invention make it possible to combat the aging of the skin affecting the epidermis, in particular for combating hydration disorders and desquamation of the epidermis, in particular those aggravated by a intense exposure to the sun, particularly when the combination product or the cosmetic composition comprises glucosamine and hyaluronic acid.

As such, said products and said compositions are useful for improving the impact and duration of cosmetic treatments based on hyaluronic acid, such as for example topical treatments, treatments using filler compositions ("fillers"), treatments using patches, etc.

They are also used elsewhere to enhance skin hydration.

In the framework of this invention, the cosmetic combination products and the cosmetic compositions according to the invention are used for the preparation of reconstructed skin and subcutaneous implants.

Consequently, this invention also relates to the use of a cosmetic combination product according to the invention or of a cosmetic composition according to the invention for combatting skin aging affecting the keratinocytes or fibroblasts, in particular against the signs of aging linked to the loss of matrix tissue or of dermal connective tissue and/or to improve the effects of cosmetic treatments based on hyaluronic acid and/or to reinforce the hydration of the skin and/or for the preparation of reconstructed skin and cutaneous implants.

The cosmetic combination products as well as the cosmetic compositions according to the invention may also be implemented in a cosmetic method for inducing the synthesis of hyaluronic acid.

As such, according to one of its aspects, this invention also relates to a cosmetic method for inducing the synthesis of hyaluronic acid, wherein a cosmetic combination product such as defined in the framework of this invention or a cosmetic composition as defined in the framework of this invention is administered, said method induces in particular the synthesis of hyaluronic acid by the keratinocytes of the skin when the cosmetic composition or cosmetic combination product comprises of glucosamine and hyaluronic acid or in particular inducing the synthesis of hyaluronic acid by the fibroblasts when the cosmetic composition or cosmetic combination product further comprises collagen.

In particular, this invention relates to a cosmetic method such as mentioned hereinabove to induce epidermal hyaluronic acid synthesis, particularly at the dermal epidermal junction.

As such, according to one of these aspects, this invention relates to a cosmetic method such as described hereinabove, for reinforcing the dermal epidermal junction and/or synthesis of connective tissue of the dermal-epidermal junction and/or for combatting skin aging affecting the keratinocytes or fibroblasts, in particular against the signs of aging linked to the loss of matrix tissue or of dermal connective tissue and/or to improve the effects of cosmetic treatments based on hyaluronic acid and/or to reinforce the hydration of the skin and/or for the preparation of reconstructed skin and cutaneous implants.

In particular, the cosmetic combination products as well as the cosmetic compositions according to the invention, in particular the combination products or cosmetic compositions comprising glucosamine, hyaluronic acid and collagen, may also be implemented in a cosmetic procedure designed to limit the appearance of wrinkles, fine lines and facial sagging, in particular to combat the reappearance of wrinkles and facial sagging after injections of hyaluronic acid in the skin, on the face and/or all areas of the body that have undergone a restorative injection procedure, aesthetic or cosmetic subsequent or concurrent, but not exceeding six months between the 2 procedures.

As such, according to one of its aspects, this invention also relates to a cosmetic method for limiting the appearance of fine lines, wrinkles and facial sagging, in particular to combat the reappearance of wrinkles and facial sagging after hyaluronic acid injections in the skin on the face and/or on all areas of the body that have undergone a restorative injection procedure, aesthetic or cosmetic subsequent or concurrent, but not exceeding six months between the two procedures, wherein a cosmetic combination product as defined in the framework of this invention or a cosmetic composition as defined in the framework of this invention, in particular a combination product or a cosmetic composition comprising glucosamine, hyaluronic acid and collagen, is administered.

Cosmetic combination products as well as cosmetic compositions according to the invention, in particular the combination products or cosmetic compositions comprising glucosamine, hyaluronic acid and collagen, may also be implemented in a cosmetic method for extending the effective life of beauty treatments made using filler compositions (filler), in particular based on hyaluronic acid injected into the skin to bridging the face, body and wrinkles.

As such, according to another of its aspects, this invention also relates to a cosmetic method to extend the duration of effectiveness of the cosmetic treatment made by filling compositions (filler), in particular based on hyaluronic acid injected into the skin to bridge the face, body and wrinkles, wherein a cosmetic combination product as defined in the framework of this invention or a cosmetic composition as defined in the framework of this invention, in particular a combination product or a cosmetic composition comprising glucosamine, hyaluronic acid and collagen, is administered.

According to an embodiment of the cosmetic method according to the invention, the cosmetic compositions of the combination product as previously described are administered orally.

According to another embodiment of the cosmetic method according to the invention, the cosmetic compositions of the combination product as previously described are administered topically.

According to yet another embodiment of the cosmetic method according to the invention, in the cosmetic combination product described hereinabove, the composition comprising glucosamine or one of the salts thereof is administered orally and the cosmetic composition(s) comprising hyaluronic acid and possibly collagen are administered topically.

According to yet another embodiment of the cosmetic method according to the invention, in the cosmetic combination products according to the invention, the composition(s) comprising hyaluronic acid and possibly collagen are intended to be administered orally and the composition comprising glucosamine or one of the salts thereof is to be administered topically.

According to a separate embodiment of the cosmetic method according to the invention, in the cosmetic combination product according to the invention, the composition comprising glucosamine or one of the salts thereof is administered orally and the cosmetic composition(s) comprising hyaluronic acid and possibly collagen is a filler cosmetic composition administered in the skin.

According to an embodiment of the cosmetic method according to the invention, in the cosmetic combination products according to the invention, the composition(s) comprising hyaluronic acid or one of the salts thereof and possibly collagen are intended to be administered orally and the composition comprising hyaluronic acid is to be administered topically.

According to another embodiment of the cosmetic method according to the invention, in cosmetic combination products according to the invention, the cosmetic composition(s) comprising glucosamine or one of the salts thereof and possibly collagen are intended to be administered orally and the composition comprising hyaluronic acid is a filler cosmetic composition intended to be administered into the skin, in particular in the framework of the preparation of fillers with hyaluronic acid.

Moreover, according to an embodiment of the cosmetic method according to the invention, the cosmetic compositions comprising glucosamine or one of the salt thereof, hyaluronic acid and possibly collagen, such as described in the framework of this invention are administered orally.

According to another embodiment of the cosmetic method according to the invention, the cosmetic compositions comprising glucosamine or one of the salt thereof, hyaluronic acid and possibly collagen, such as described in the framework of this invention are administered topically.

In the description, the ranges of values written as "between . . . and . . . " include the lower and upper limits specified.

Further features and advantages of the invention will emerge from the examples hereinafter, given by way of illustration and not limiting.

FIGURES

FIG. 1: Synergistic effect of glucosamine sulfate and hyaluronic acid on the production of hyaluronic acid by NHEK cells (Normal Human Epidermal Keratinocytes): four series of results are shown (from left to right) which represent:

$1^{st}$ series: hyaluronic acid production by NHEK cells obtained by means of the combination of glucosamine sulfate and hyaluronic acid in the following proportions of glucosamine sulphate (μg/ml) Hyaluronic-acid (ng/ml) (left to right): 0.25 to 25 μg/ml-40 to 6000 ng/ml;

$2^{nd}$ series: hyaluronic acid production by NHEK cells obtained by hyaluronic acid alone in the proportion of hyaluronic acid (ng/ml) (from left to right): 40 to 6000 ng/ml;

$3^{th}$ series: hyaluronic acid production by NHEK cells obtained by means of one glucosamine sulfate in the proportion of glucosamine sulfate (ug/ml) (left to right): 0.25 to 25 μg/ml; et $4^{th}$ series: RA control.

Figure 2:
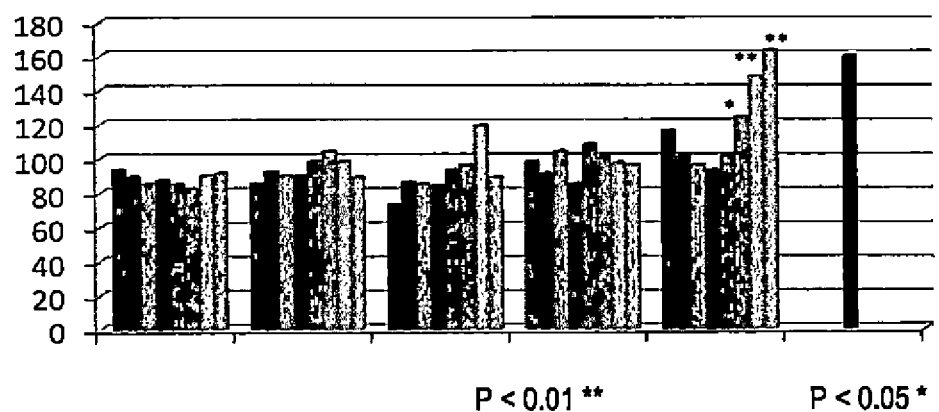

FIG. 2: Synergistic effect of glucosamine sulfate, hyaluronic acid and collagen on the production of hyaluronic acid by NHDF cells (Normal Human Dermal Fibroblasts): six sets of results are shown (from left to right) representing:

$1^{st}$ series: hyaluronic acid production by NHDF cells obtained by means of one glucosamine sulfate in the proportion of glucosamine sulfate (ug/ml) (left to right): 0.1 to 100 μg/ml;

$2^{nd}$ series: hyaluronic acid production by NHDF cells obtained by hyaluronic acid alone in the proportion of hyaluronic acid (ng/ml) (from left to right): 40 to 6000 ng/ml;

$3^{rd}$ series: hyaluronic acid production by NHDF cells obtained by means of the combination of glucosamine sulfate and hyaluronic acid in the following proportions of glucosamine sulphate (µg/ml) and hyaluronic acid (ng/ml) (from left to right): 0.1 to 100 µg/ml and 40 to 6000 ng/ml;

$4^{th}$ series: hyaluronic acid production by NHDF cells obtained by means of the combination of hyaluronic acid source and collagen only in the following proportions (ng/ml): 4 to 4000 ng/ml;

$5^{th}$ series: hyaluronic acid production by NHDF cells obtained by means of the combination of glucosamine sulfate and a hyaluronic acid and collagen source in the following proportions of glucosamine sulphate (µg/ml) and source of hyaluronic acid and collagen (ng/ml): 0.1 to 100 µg/ml and 4 to 4000 ng/ml; and $6^{th}$ series: TGF-beta control.

EXAMPLES

Example 1: Synergistic Effect of Glucosamine Sulfate and Hyaluronic Acid on the Production of Hyaluronic Acid by NHEK Cells Normal human epidermal keratinocytes were cultured at 37° C. under 5% $CO_2$ in a medium keratinocyte-SFM culture, supplemented with epidermal growth factor (EGF; 0.25 ng/ml), a pituitary extract (25 µg/ml) and an antibiotic (gentamicin 25 µg/ml) in 96-well plates for 24 h without stimulation.

Glucosamine and/or hyaluronic acid are then added to the cultivation medium alone or in combination at concentrations of 40 to 6000 ng/ml hyaluronic acid and 0.25 to 25 µg/ml to glucosamine sulfate. After 72 hours of cultivation under these conditions, the supernatant was collected to quantify the hyaluronic acid produced by the cells using an ELISA Duoset Hyaluronan kit marketed by the company R & D System (DY3614 reference).

The results obtained and presented in FIG. 1 show an induction of hyaluronic acid production by human keratinocytes in vitro, obtained by means of only glucosamine sulfate.

They also demonstrate that contact of keratinocytes with hyaluronic acid alone does not stimulate the synthesis of hyaluronic acid.

However, a synergistic induction of hyaluronic acid production by human keratinocytes in vitro, is clearly obtained by combining glucosamine sulfate and hyaluronic acid.

Indeed, the observed results allow to conclude here to a synergistic effect between glucosamine sulfate and hyaluronic acid in comparison with the results obtained with each of the compounds alone, with an increased effect of 246% ($p<0.001$).

Example 2: Synergistic Effect of Glucosamine Sulfate, Hyaluronic Acid and Collagen on the Synthesis of Hyaluronic Acid Normal human dermal fibroblasts (NHDF) were cultured at 37° C. under 5% $CO_2$ in a DMEM culture medium supplemented with glutamine (2 mM); calf serum (1%), penicillin (50 U/ml) and streptomycin (50 mg/ml).

Glucosamine (0.1 to 100 µg/ml) and/or hyaluronic acid (from 40 to 6000 ng/ml) and/or a source of collagen and hyaluronic acid (in a ratio of between 0.07% and 15%) at concentrations ranging from 4 to 4000 ng/ml were then added to the cultivation medium alone or in combination.

After 72 hours of cultivation under these conditions, the supernatant was collected to quantify the hyaluronic acid produced by the cells using an ELISA Duoset Hyaluronan kit marketed by the company R & D System (DY3614 reference).

The results obtained and presented in FIG. 2 show that the synergistic induction of hyaluronic acid production by human fibroblasts in vitro, is clearly obtained by combining glucosamine sulfate, hyaluronic acid and collagen.

Indeed, the results observed allow to conclude here to a synergistic effect between glucosamine sulfate, hyaluronic acid and collagen compared to the lack of stimulation obtained by administering only glucosamine sulfate or natural cartilage extract alone comprising hyaluronic acid and collagen or the combination only hyaluronic acid and glucosamine.

The invention claimed is:

1. A method to induce the synthesis of hyaluronic acid which comprises administering orally or topically or both to an individual in need thereof; a cosmetic product combination comprising
   a first cosmetic composition comprising from 0.1% to 10% by weight of glucosamine sulfate, a second cosmetic composition comprising at least 4% by weight of hyaluronic acid and a third cosmetic composition comprising from 0.1% to 10'1% by weight of collagen,
   or a cosmetic composition comprising from 0.1% to 10% by weight of glucosamine sulfate, at least 4% by weight of hyaluronic acid and from 0.1% to 10% by weight of collagen,
   wherein the glucosamine sulfate, hyaluronic acid and collagen exhibit synergistic synthesis of hyaluronic acid by fibroblasts.

2. The method according to claim 1, for inducing epidermal hyaluronic acid synthesis, wherein the administering is to an individual in need thereof.

3. The method according to claim 1, for enhancing the synthesis of hyaluronic acid in the dermis and connective tissue of the dermal epidermal junction, wherein the administering is to an individual in need thereof.

4. The method according to claim 1, for combatting the signs of aging linked to the loss of connective tissue and skin, wherein the administering is to an individual in need thereof.

5. The method according to claim 1, for combatting the signs of aging linked to the loss of matrix tissue, dryness and dry and thin appearance of the skin, wherein the administering is to an individual in need thereof.

6. The method according to claim 1, for combatting the signs of aging linked to the loss of matrix tissue, the appearance of lines and wrinkles and sagging skin, wherein the administering is to an individual in need thereof.

7. The method according to claim 1, for combatting skin aging affecting the skin, wherein the administering is to an individual in need thereof.

8. The method according to claim 1, for enhancing the effects and duration of cosmetic treatment based on hyaluronic acid, wherein the administering is to an individual in need thereof.

9. The method according to claim 1, for enhancing skin hydration, wherein the administering is to an individual in need thereof.

10. The method according to claim 1, for preparing reconstructed skin and subcutaneous implants, wherein the administering is to an individual in need thereof.

11. The method according to claim 1, wherein said second cosmetic composition comprising hyaluronic acid and said third cosmetic composition comprising collagen constitute one cosmetic composition wherein the hyaluronic acid and collagen are derived from a cartilage extract.

12. The method according to claim 1, wherein the hyaluronic acid is of biotechnological origin.

13. The method according to claim 1, wherein the collagen is derived from a purification method from fish, mammal or poultry.

14. The method according to claim 1, wherein said compositions are administered orally.

15. The method according to claim 1, wherein said compositions are administered topically.

16. The method according to claim 1, wherein the composition comprising glucosamine sulfate is administered orally and the compositions comprising hyaluronic acid and/or collagen are administered topically.

17. The method according to claim 1, wherein the composition comprising hyaluronic acid and/or collagen are administered by the oral route and the composition comprising glucosamine sulfate is administered topically.

18. The method according to claim 1, wherein the compositions comprising glucosamine sulfate and/or collagen are administered orally and the composition comprising hyaluronic acid is administered topically.

19. The method according to claim 1, wherein the cosmetic combination product comprises 0 to 30% hyaluronic acid.

20. The method according to claim 1 wherein the cosmetic combination product is a cosmetic composition comprising
glucosamine sulfate, hyaluronic acid and collagen.

21. The method according to claim 20, wherein the hyaluronic acid and collagen are derived from a cartilage extract.

22. The method according to claim 20, wherein the hyaluronic acid is of biotechnological origin.

23. The method according to claim 20, wherein the cosmetic composition is administered orally.

24. The method according to claim 20, wherein the cosmetic composition is administered topically.

25. The method according to claim 20, wherein the cosmetic composition comprises 0 to 30% hyaluronic acid.

26. A cosmetic method for inducing the synthesis of hyaluronic acid, wherein a cosmetic product combination comprising
a first cosmetic composition comprising from 0.1% to 10% by weight of glucosamine sulfate, a second cosmetic composition comprising at least 4% by weight of hyaluronic acid and a third cosmetic composition comprising from 0.1% to 10% by weight of collagen,
or a cosmetic composition comprising from 0.1% to 10% by weight of glucosamine sulfate, at least 4% by weight of hyaluronic acid hyaluronic acid and from 0.1% to 10% by weight of collagen is administered orally or topically or both to an individual in need thereof,
the glucosamine sulfate, hyaluronic acid and collagen exhibit synergistic synthesis of hyaluronic acid by fibroblasts.

27. The cosmetic method according to claim 26, to combat the reappearance of wrinkles and facial sagging after injections of hyaluronic acid in the skin on the face and/or on all body parts that have been the subject of a restorative injection procedure, aesthetic or cosmetic subsequent or concurrent, but not exceeding six months between the 2 procedures.

28. A cosmetic method for limiting the appearance of fine lines, wrinkles and facial sagging by inducing the synthesis of hyaluronic acid, wherein a cosmetic product combination comprising
a first cosmetic composition comprising from 0.1% to 10% by weight of glucosamine sulfate, a second cosmetic composition comprising at least 4% by weight of hyaluronic acid hyaluronic acid and a third cosmetic composition comprising from 0.1% to 10% weight of collagen,
or a cosmetic composition comprising from 0.1% to 10% b weight of glucosamine sulfate, at least 4% by weight of hyaluronic acid and from 0.1% to 10% by weight of collagen is administered orally or topically or both to an individual in need thereof,
wherein the glucosamine sulfate, hyaluronic acid and collagen exhibit synergistic synthesis of hyaluronic acid by fibroblasts.

29. A cosmetic method for extending the duration of efficacy of beauty treatments made using filler compositions (filler) by inducing the synthesis of hyaluronic acid, wherein a cosmetic product combination comprising
a first cosmetic composition comprising from 0.1% to 10% by weight of glucosamine sulfate, a second cosmetic composition comprising at least 4% by weight of hyaluronic acid hyaluronic acid and a third cosmetic composition comprising from 0.1% to 10% by weight of collagen,
or a cosmetic composition comprising from 0.1% to 10% by weight of glucosamine sulfate, at least 4% by weight of hyaluronic acid and from 0.1% to 10% by weight of collagen is administered orally or topically or both, to an individual after having a beauty treatment,
wherein the glucosamine sulfate, hyaluronic acid and collagen exhibit synergistic synthesis of hyaluronic acid by fibroblasts.

* * * * *